United States Patent
Keller et al.

(10) Patent No.: US 10,213,181 B2
(45) Date of Patent: Feb. 26, 2019

(54) STETHOSCOPE DIAPHRAGM

(71) Applicant: 3M INNOVATIVE PROPERTIES COMPANY, St. Paul, MN (US)

(72) Inventors: Joseph P. Keller, Wahpeton, ND (US); Mary Jo Johnson, Lake Elmo, MN (US); Dean E. Sitz, Wahpeton, ND (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 23 days.

(21) Appl. No.: 15/544,304

(22) PCT Filed: Jan. 12, 2016

(86) PCT No.: PCT/US2016/012945
§ 371 (c)(1),
(2) Date: Jul. 18, 2017

(87) PCT Pub. No.: WO2016/118356
PCT Pub. Date: Jul. 28, 2016

(65) Prior Publication Data
US 2018/0008227 A1    Jan. 11, 2018

Related U.S. Application Data

(60) Provisional application No. 62/105,898, filed on Jan. 21, 2015.

(51) Int. Cl.
*A61B 7/02* (2006.01)
*A61B 7/00* (2006.01)
*G10K 11/18* (2006.01)

(52) U.S. Cl.
CPC ...................... *A61B 7/02* (2013.01)

(58) Field of Classification Search
CPC .. A61B 7/00; A61B 7/02; A61B 7/026; G10K 11/18
See application file for complete search history.

(56) References Cited

U.S. PATENT DOCUMENTS

| 4,200,169 A | 4/1980 | MacDonald, III |
| 4,440,258 A | 4/1984 | Packard |
| 4,461,368 A * | 7/1984 | Plourde ................ A61B 7/02 181/131 |
| 4,475,619 A | 10/1984 | Packard |
| 4,770,270 A | 9/1988 | Grimm |
| 4,852,684 A | 8/1989 | Packard |
| 4,913,259 A | 4/1990 | Packard |

(Continued)

FOREIGN PATENT DOCUMENTS

| CN | 201409932 | 2/2010 |
| CN | 201409933 | 2/2010 |

(Continued)

OTHER PUBLICATIONS

International Search Report for PCT International Application No. PCT/US2016/012945, dated Apr. 28, 2016, 3 pages.

*Primary Examiner* — Edgardo San Martin
(74) *Attorney, Agent, or Firm* — 3M Innovative Properties Company; Jonathan V. Sry

(57) ABSTRACT

The present invention is a stethoscope diaphragm including a disc and a rim. The rim includes a plurality of features extending from an inner circumference of the rim.

14 Claims, 6 Drawing Sheets

(56) References Cited

U.S. PATENT DOCUMENTS

| | | | |
|---|---|---|---|
| 4,995,473 A * | 2/1991 | Packard | A61B 7/02 181/131 |
| 5,111,904 A | 5/1992 | Packard | |
| 5,324,471 A | 6/1994 | Packard | |
| 5,380,182 A | 1/1995 | Packard | |
| 5,449,865 A | 9/1995 | Desnick | |
| 5,616,890 A * | 4/1997 | Boussignac | A61B 7/026 181/131 |
| 5,796,053 A * | 8/1998 | Shieh | A61B 7/02 181/131 |
| 5,910,992 A * | 6/1999 | Ho | A61B 7/026 181/131 |
| 5,921,941 A | 7/1999 | Longobardo | |
| 5,931,792 A * | 8/1999 | Packard | A61B 7/026 181/131 |
| 5,932,849 A * | 8/1999 | Dieken | A61B 7/04 181/131 |
| 5,945,640 A | 8/1999 | Rossini | |
| 6,019,187 A * | 2/2000 | Appavu | A61B 7/02 181/131 |
| 6,244,376 B1 * | 6/2001 | Granzotto | A61B 7/02 181/131 |
| 6,378,648 B1 | 4/2002 | Werblud | |
| 6,523,639 B1 | 2/2003 | Shieh | |
| 7,757,807 B1 | 7/2010 | Martinez | |
| 9,770,307 B2 * | 9/2017 | Krupnick | A61B 7/02 |
| 2009/0211838 A1 | 8/2009 | Bilan | |

FOREIGN PATENT DOCUMENTS

| | | | |
|---|---|---|---|
| CN | 203244411 | 10/2013 | |
| CN | 203354564 | 12/2013 | |
| DE | 212013000288 U1 * | 11/2015 | A61B 7/02 |
| WO | WO 2016022380 | 2/2016 | |

* cited by examiner

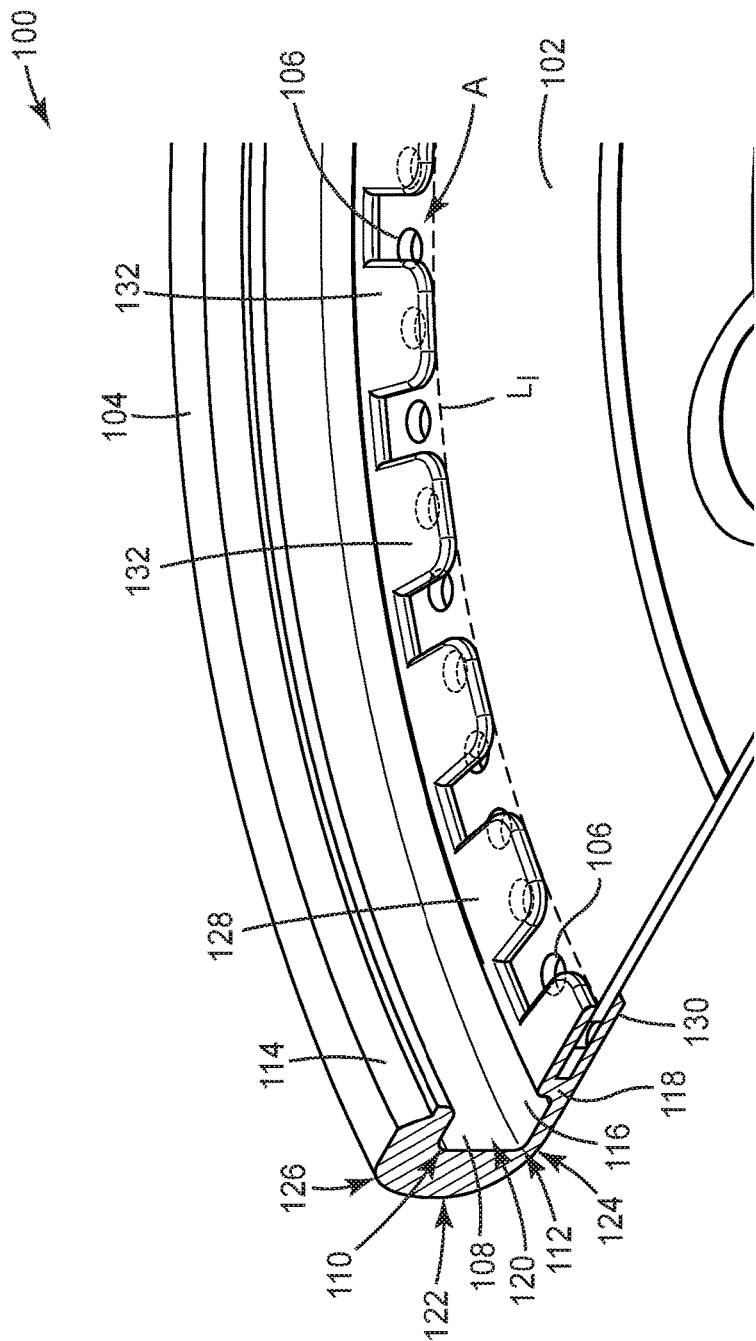

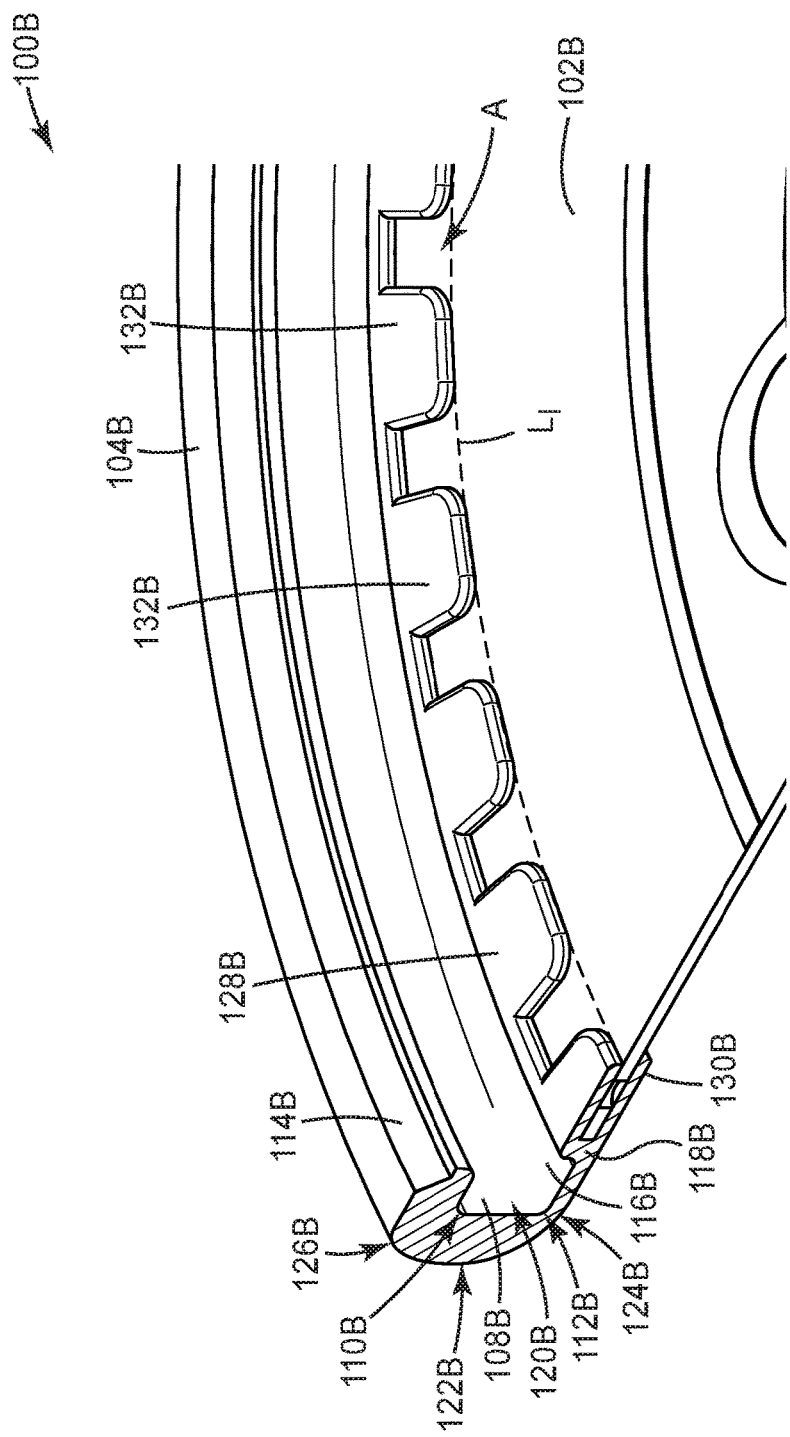

STETHOSCOPE DIAPHRAGM

CROSS REFERENCE TO RELATED APPLICATIONS

This application is a national stage filing under 35 U.S.C. 371 of PCT/US2016/012945, filed Jan. 12, 2016, which claims the benefit of U.S. Provisional Application No. 62/105,898, filed Jan. 21, 2015, the disclosure of which is incorporated by reference in its/their entirety herein.

FIELD OF THE INVENTION

The present invention is related generally to the field of stethoscopes. In particular, the present invention is related to stethoscope diaphragms having a series of features.

BACKGROUND

Complete diagnosis of a patient using a stethoscope often requires that a physician monitor low frequency and high frequency sounds associated with, for example, the heart. With respect to the heart, it is important that the physician alternate between the monitoring of low frequency and high frequency sounds so that the physician does not lose the impression from the previously heard heartbeat before the next beat is heard. Without the benefit of tunable technology, the clinician would be required to turn the chestpiece over to hear additional sounds. The diaphragms currently used on most stethoscopes include two pieces, the diaphragm and the rim. These pieces may be manufactured as two separate pieces or as a single, unitary piece. The rim is used to hold the diaphragm on the chestpiece.

SUMMARY

In one embodiment, the present invention is a stethoscope diaphragm including a disc and a rim. The rim includes a plurality of features extending from an inner circumference of the rim.

In another embodiment, the present invention is a stethoscope diaphragm including a disc and a rim. The rim includes a wall having a first end and a second end; a lip extending substantially perpendicularly from the first end of the wall; a bridge extending substantially perpendicularly from the second end of the wall; a fork extending from the bridge, wherein the fork includes an inner flange and an outer flange; and a plurality of features extending from the inner flange.

BRIEF DESCRIPTION OF THE DRAWINGS

These figures are not drawn to scale and are intended merely for illustrative purposes.

FIG. 5A is an enlarged view of a portion of the first embodiment of the diaphragm of the present invention shown in FIG. 4A.

FIG. 5B is an enlarged view of a portion of the second embodiment of the diaphragm of the present invention shown in FIG. 4B.

DETAILED DESCRIPTION

The present invention is a diaphragm to be used with stethoscopes. In one embodiment, the stethoscopes are tunable stethoscopes. The diaphragm includes a disc and a rim. The rim includes a plurality of features extending from the inner circumference of the rim which surrounds the underside of the disc. The plurality of features adds support to the disc and provides a uniform part. In addition, the diaphragm including the rim having the plurality of features allows for the diaphragm to be manufactured with a decreased number of defects.

As used in the instant specification and claims, "acoustical stiffness" of the diaphragm designates the mechanical stiffness of the diaphragm as influenced by the mechanical stiffness of the diaphragm material itself, the thickness of the diaphragm, the shape of the diaphragm, the diameter of the diaphragm, and the manner in which the diaphragm is attached to the stethoscope head. The phrase "plane of the diaphragm" refers to the generally planar surface of the diaphragm (disc).

As used in the instant specification and claims, the phrase "suspended diaphragm" designates a diaphragm having at least a suspension member as described below. The diaphragm and suspension member are operatively associated with an immobilization means as described below. For example, the suspended diaphragm may be constructed according to the teachings of U.S. Pat. No. 4,440,258 to Packard (the entire contents of which are herein incorporated by reference).

Figures 1, 2:
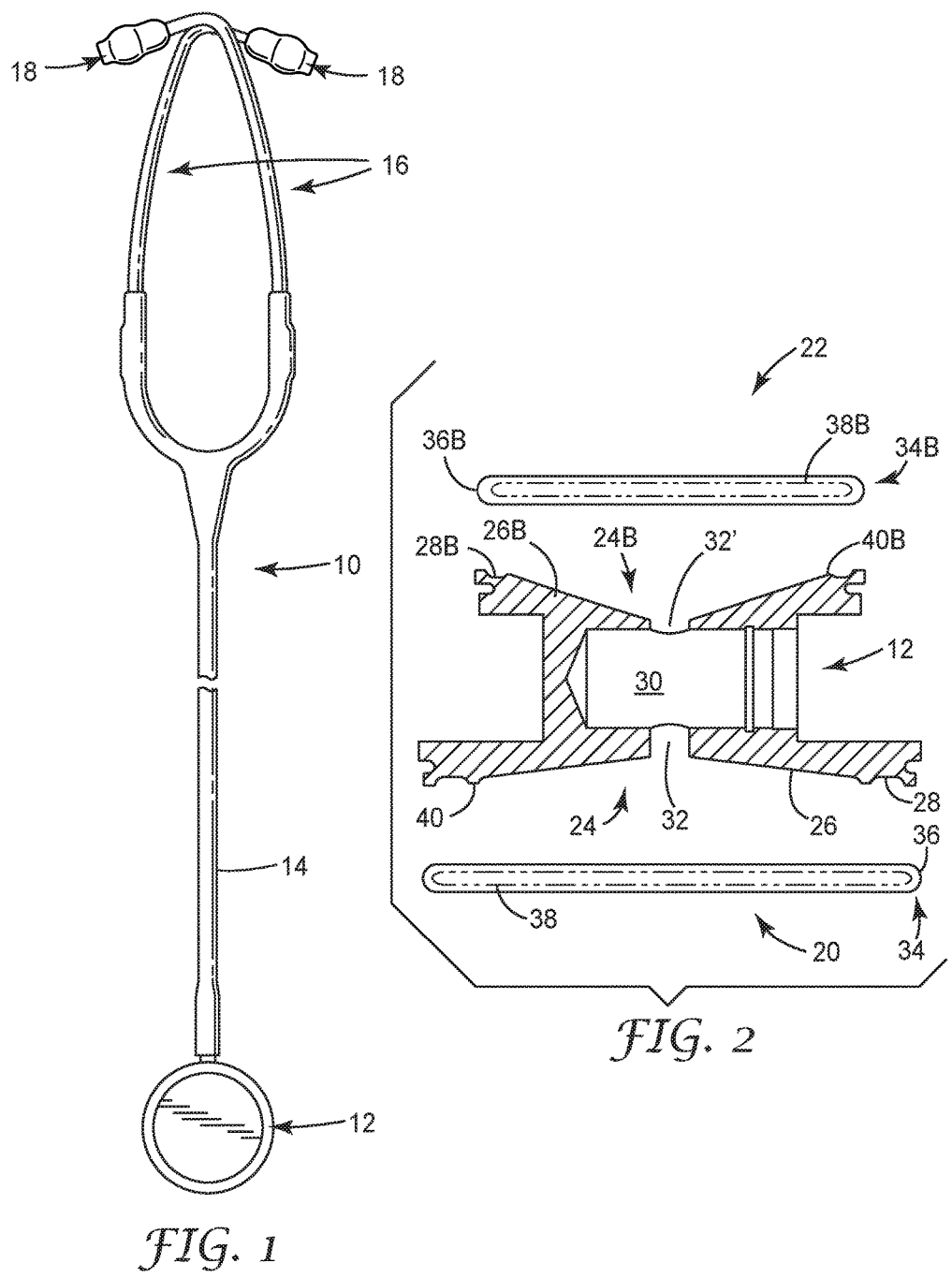
FIG. 1 is a schematic view of a stethoscope using a diaphragm according to the present invention.
FIG. 2 is an enlarged, exploded, partial sectional view of a chestpiece of the stethoscope of FIG. 1.

Referring first to FIG. 1, a stethoscope 10 includes a chestpiece 12 formed of conventional material utilized in the fabrication of stethoscope chestpieces, for example, metals such as stainless steel and aluminum, metallic composites, plastic and wood. The chestpiece 12 is attached to a conventional headset such as that described in U.S. Pat. No. 4,200,169 which includes an elongated flexible tubing 14 that splits into flexible tubings 16 that run to ear tips 18. The lower end of the flexible tubing 14 is adapted to be coupled to a conventional stem fitting on the chestpiece 12. The coupling may utilize the indexing detent as taught in U.S. Pat. No. 4,770,270 (the entire contents of which are herein expressly incorporated by reference). Binaural tubes for stethoscopes can be prepared in accordance with the teachings of U.S. Pat. Nos. 5,111,904; 5,380,182; and U.S. Pat. No. 5,324,471 to Packard et al. (each of which is hereby incorporated by reference).

The ear tips 18 are sized and shaped to engage the surfaces of the user's ears. The ear tips 18 may include any suitable ear tips. In one embodiment, the ear tips 18 include the soft ear tips disclosed in U.S. Pat. Nos. 4,852,684; 4,913,259 and 5,449,865 (the entire contents hereby incorporated by reference).

Figure 3A:
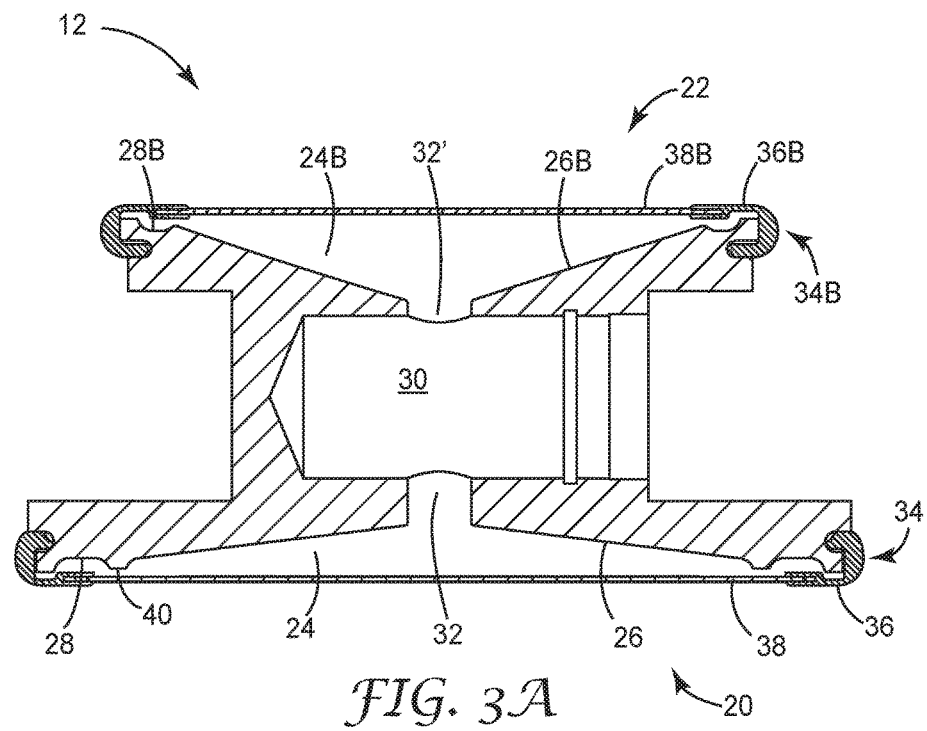
FIG. 3A is a cross-sectional view of an assembled chestpiece showing a diaphragm of the present invention in an outer position.
Figure 3B:
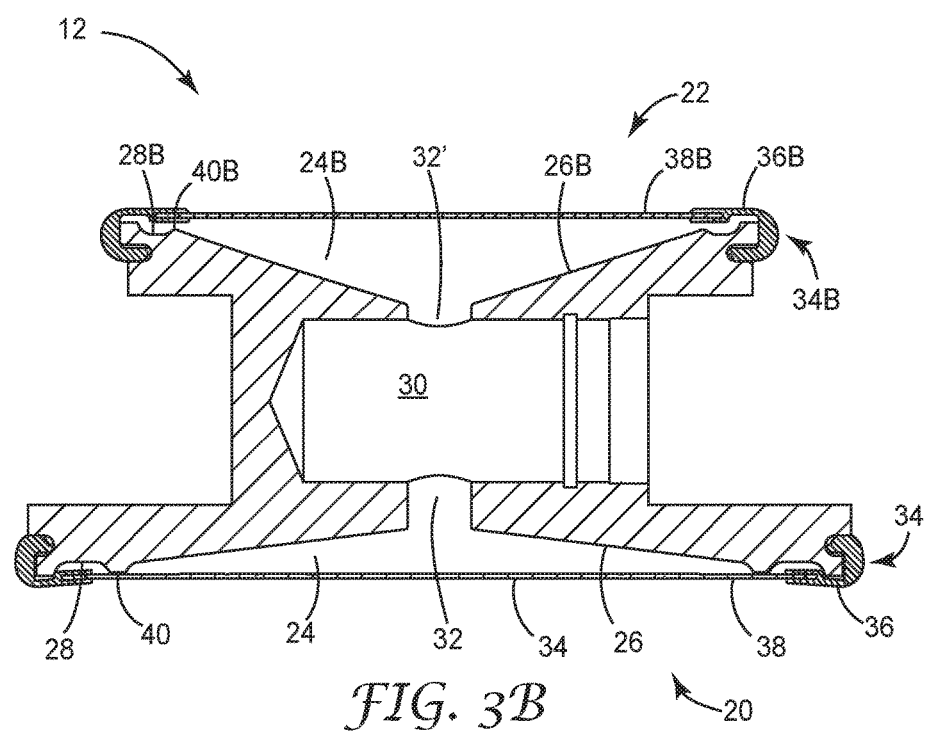
FIG. 3B is a cross-sectional view of an assembled chestpiece showing a diaphragm of the present invention in an inner position.

Referring to one embodiment shown in FIGS. 2, 3A and 3B, the chestpiece 12 is a dual-sided chestpiece including a first sound collecting side 20 and a second sound collecting side 22. It should be noted that although the diaphragm of the present invention is discussed with respect to a dual-sided chestpiece, the diaphragm may also be used with a single-sided chestpiece without limiting the scope of the present invention. In one embodiment, the stethoscope 10 affords tuning in of sound while using either the first side 20 or the second side 22 of the chestpiece 12. The first sound collecting side 20 is sized and shaped to collect sounds from adult patients. The second sound collecting side 22 is sized and shaped to afford sufficient surface contact on pediatric or thin patients. The second sound collecting side 22 is also substantially smaller than the first sound collecting side to afford easier access to remote or difficult to reach locations.

The first sound collecting side 20 has a first recess 24 with an innermost central portion 26, an outer rim portion 28, and an acoustic channel 30, 32 communicating with the central portion 26. A first diaphragm 34 is also located on the first sound collecting side 20. The first diaphragm 34 includes a rim 36 and disc 38 positioned within the rim 36, together having a peripheral edge portion and a predetermined surface contour overlying at least a portion of the first recess 24. As shown in FIGS. 3A and 3B, the first diaphragm 34 is moveably connected to or "operatively associated" with the outer rim portion 28 of the first recess 24.

The first diaphragm 34 is positioned on the chestpiece 12 such that there can be movement of the first diaphragm 34 in a direction substantially perpendicular to the plane of the first diaphragm 34 between: 1) a normal outer position to which the first diaphragm 34 is biased and 2) an inner position more closely adjacent the central portion of the first recess 24. This movement is accomplished without substantially changing the surface contour of or the lateral tension in the first diaphragm 34.

A first immobilizing means 40 is situated on the first sound collecting side 20 of the chestpiece 12. The first immobilizing means 40 is located within the first recess 24. Together with the central portion of the first recess 24, the first immobilizing means 40 forms a shallow recess within the first recess 24. The immobilizing means 40 is sized and shaped to be contacted by the first diaphragm 34. In FIG. 3B, it is the first diaphragm 34 which contacts the immobilizing means 40. When the first diaphragm 34 is in the inner position, the immobilizing means 40 immobilizes the first diaphragm 34.

The first sound collecting side 20 of the chestpiece 12 will pass low frequency (bass) sounds and gradually attenuate sounds with higher frequencies when the first diaphragm 34 is in the outer position and between the outer and inner positions. When the first diaphragm 34 is in the inner position, the acoustical stiffness of the first diaphragm 34 will be significantly higher than the acoustical stiffness of the first diaphragm 34 when it is in the outer position, so that the first sound collecting side 20 of the chestpiece 12 will attenuate or block low frequency sounds while leaving higher frequency sounds unchanged. In use, a physician would simply modify the manual pressure exerted on the chestpiece 12 in order to switch between the outer and inner positions. In one embodiment, the level of bass attenuation varies from about 3 to about 21 dB.

The second sound collecting side 22 is adapted to include a second suspended diaphragm. The second sound collecting side 22 has many reference characters similar to the reference characters used to describe elements of the first sound collecting side 20 except that the reference character "B" has been added. The second sound collecting side 22 has a second recess 24B with an innermost central portion 26B, an outer rim portion 28B, and an acoustic channel 30, 32' communicating with the central portion 26B. The second sound collecting side 22 has a second diaphragm 34B including a rim 36B and disc 38B positioned within the rim 36B, together having with a peripheral edge portion and a predetermined surface contour overlying at least a portion of the second recess 24B. The second diaphragm 34B is moveably associated with the outer rim portion 28B of the second recess 24B.

A second immobilizing means 40B is situated on the second sound collecting side 22 of the chestpiece 12. The second immobilizing means 40B is located within the second recess 24B. Together with the central portion 26B of the second recess 24B, the second immobilizing means 40B forms a shallow recess within the second recess 24B. The second immobilizing means 40B is sized and shaped to be contacted by the second diaphragm 34B. When the second diaphragm 34B is in the inner position, the second immobilizing means 40B immobilizes the second diaphragm 34B.

The second sound collecting side 22 of the chestpiece 12 will pass low frequency sounds and gradually attenuate sounds with higher frequencies when the second diaphragm 34B is in the outer position and between the outer and inner positions. When the second diaphragm 34B is in the inner position, the acoustical stiffness of the second diaphragm 34B will be significantly higher than its first acoustical stiffness so that the second sound collecting side 22 of the chestpiece 12 will attenuate or block low frequency sounds while leaving higher frequency sounds unchanged. In one embodiment, the level of bass attenuation varies from about 3 to about 21 dB.

The size and shape of the first sound collecting side 20 is different than the size and shape of the second sound collecting side 22.

In one embodiment, the immobilizing means 40 and 40B include ridges machined into the metal of the chestpiece 12 (see FIGS. 3A and 3B). Other immobilizing means which are suitable for employment in the stethoscope heads of the present invention include O-rings, molded ridges, and inserts (e.g., plastic inserts). For example, the machined ridge 40B may have an inner diameter of about 1.053 inches, a depth radius of about 0.016 inches (0.41 millimeters), and a width of 0.015 inches (0.38 millimeters).

The diaphragms 34 and 34B overlay their respective recesses 24 and 24B sufficiently to afford contact of the diaphragms with the immobilizing means 40 and 40B. The rims 36 and 36B and discs 38 and 38B of diaphragms 34 and 34B may comprise any material which is known in the art as being suitable for use as a diaphragm. Examples of suitable materials include silicone, urethane, polymeric resin material, plastics such as polyester, fiberglass-reinforced plastics and polystyrene and metals such as stainless steel. A suitable thickness for the diaphragms 34 and 34B, measured at the thickest cross section of the rim 36, 36B, is about 0.08 to 0.31 inches (2.03 to 7.87 millimeters). A particularly suitable diaphragm includes a 0.110 inch-thick (2.79 millimeter-thick) epoxy resin-fiberglass laminate, generally available from Innovize located in St. Paul, Minn. Although the figures depict the diaphragms 34 and 34B as being circular, the diaphragms may take any shape without departing from the intended scope of the present invention. For example, the diaphragms may have an oval or tear-drop shape.

The response of chestpiece 12 to low frequency and high frequency sounds is affected by several parameters. The thickness of the diaphragm affects the response, and suitable thicknesses for the diaphragms have been discussed hereinabove. Also, the relative dimensions of first recess and second recess affect the response. The following have been found to be suitable dimensions for the recess 24B: the recess 24B has a diameter of about 1.32 inches (3.35 centimeters), a major radius as seen in FIGS. 3A and 3B of about 0.196 inches (4.98 millimeters), an initial major depth of about 0.22 inches (5.6 millimeters) and a secondary depth of about 0.235 inches (5.97 millimeters). The passage 32' has a diameter of about 0.125 inches (3.175 millimeters).

It is contemplated that the acoustical stiffness of the diaphragm can be increased suitably by contact of the suspension member with the immobilizing means.

Figure 4A:
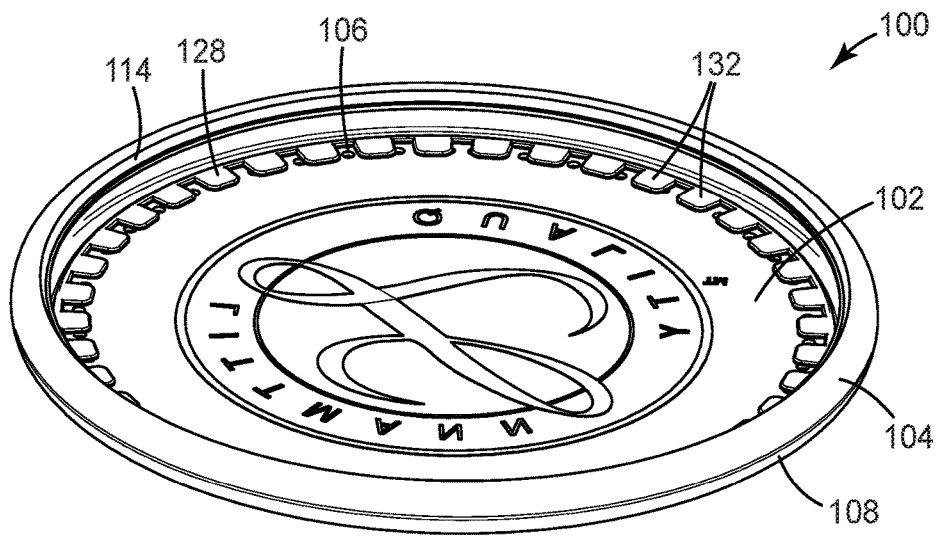
FIG. 4A is a perspective view of a first embodiment of a diaphragm of the present invention.
Figure 4B:
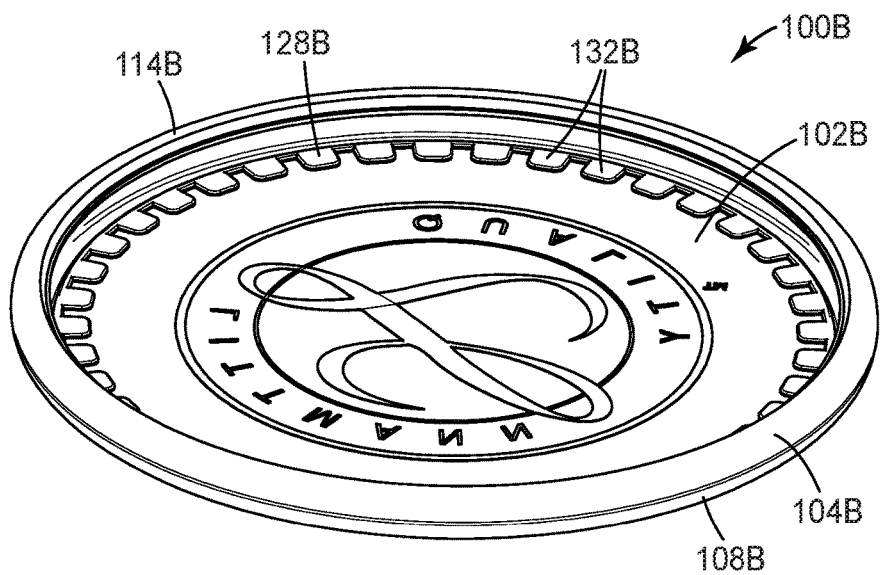
FIG. 4B is a perspective view of a second embodiment of a diaphragm of the present invention.

Turning now to FIGS. 4A and 5A and 4B and 5B, first and second embodiments, respectively, of the diaphragm 100 and 100B of the present invention will be described in more detail. FIG. 4A shows a perspective view of a first embodiment of the diaphragm 100 and FIG. 5A shows an enlarged view of a portion of the first embodiment of the diaphragm 100. FIG. 4B shows a perspective view of a second embodiment of the diaphragm 100B and FIG. 5B shows an enlarged view of a portion of the second embodiment of the diaphragm 100B. The second embodiment of the diaphragm 100B has many reference characters similar to the reference characters used to describe elements of the first embodiment of the diaphragm 100 except that the reference character "B" has been added. The elements otherwise function similarly. As mentioned above, the diaphragm 100, 100B includes a disc 102, 102B and a rim 104, 104B. In one embodiment, the disc 102, 102B and the rim 104, 104B are made from different materials but can be a unitary piece when fabricated. In another embodiment, the disc 102, 102B and the rim 104, 104B are made of the same material.

The disc 102, 102B may be formed of any material which is known in the art as being suitable for use as a diaphragm disc. Examples of suitable materials include plastics such as polyester, fiberglass-reinforced plastics, polycarbonates, carbon fiber composites, polystyrene and metals such as stainless steel. A suitable thickness for the disc 102, 102B is about 0.005 to about 0.020 inches (127 to 508 micrometer) and particularly about 0.010 to about 0.012 inches (254 to 305 micrometer). In one embodiment, the disc 102, 102B is a 0.010 inches thick (254 micrometer-thick) epoxy resin-fiberglass laminate.

In the first embodiment of the diaphragm 100 shown in FIGS. 4A and 5A, the disc 102 includes a plurality of apertures 106 along the periphery of the disc 102. The apertures 106 aid in maintaining the disc 102 to the rim 104 during molding and long term use of the diaphragm 100. In the unitary molding process, the disc 102 is placed in the diaphragm rim die tool (for example an injection mold). The material used for the rim is then melt molded (for example injection molded) around the edge of the diaphragm disc to form a unitary single piece diaphragm which includes the rim.

Although FIGS. 4A and 5A show the disc 102 as having a plurality of apertures 106, the disc 102 may include any number of apertures 106, including only one, along a periphery of the disc 102 without departing from the intended scope of the present invention. In the second embodiment shown in FIGS. 4B and 5B, the diaphragm 100B does not include any apertures in the disc 102B.

Looking particularly at FIGS. 5A and 5B, the rim 104, 104B includes a wall 108, 108B having a first end 110, 110B and a second end 112, 112B, a lip 114, 114B extending substantially perpendicularly from the first end 110, 110B of the wall 108, 108B, a bridge 116, 116B extending substantially perpendicularly from the second end 112, 112B of the wall 108, 108B, and a fork 118, 118B extending from the bridge 116, 116B.

The wall 108, 108B has a circular or ring-shaped configuration and functions to maintain the diaphragm 100, 100B on the chestpiece 12. The wall 108, 108B has an inner side 120, 120B and an opposite outer side 122, 122B, a patient facing edge 124, 124B and an opposite chestpiece facing edge 126, 126B. The wall 108, 108B must be thick enough to have sufficient rigidity to stay on the chestpiece 12. If the wall 108, 108B is too thick, the diaphragm 100, 100B may fall off of the chestpiece 12 (FIG. 1) when a small amount of pressure is applied. For example, if the wall is too thick, when the chestpiece rubs on clothing, such as when a health care provider removes the chestpiece from a pocket, the diaphragm may unintentionally fall off of the chestpiece. The height of the wall 108, 108B is important in determining the height of the disc 102, 102B above the chestpiece 12, which in turn affects tunability of the chestpiece 12.

The lip 114, 114B extends from the inner side 120, 120B at the first end 110, 110B of the wall 108, 108B at the chestpiece facing edge 126, 126B and functions to secure the diaphragm 100, 100B to the chestpiece 12. When assembled, the chestpiece 12 is inserted between the lip 114, 114B and the fork 118, 118B of the rim 104, 104B. The lip 114, 114B must hold the diaphragm 100, 100B tightly enough to stay on the chestpiece 12, but not so tight such that the diaphragm 100, 100B cannot be removed if desired, for example, for cleaning.

The bridge 116, 116B extends from the inner side 120, 120B of the second end 112, 112B of the wall 108, 108B at the patient facing edge 124, 124B. The bridge 116, 116B, and particularly the bridge height and thickness, allows the diaphragm 100, 100B to have sufficient flexibility to move and achieve good acoustics. The bridge height needs to be as thin as possible while minimizing the risk of the rim 104, 104B breaking during normal use. The bridge width should be as long as possible between the chestpiece outer diameter contact surface and the disc while still allowing filling during molding.

The fork 118, 118B extends from the bridge 116, 116B and functions to secure the disc 102, 102B within the rim 104, 104B and includes an inner flange 128, 128B and an outer flange 130, 130B substantially perpendicular to the inner flange 128, 128B. The disc 102, 102B is positioned between the inner and outer flanges 128, 128B and 130, 130B, where it is maintained within the rim 104, 104B. The fork flanges 128, 128B and 130, 130B need to be thick enough to allow filling on both sides of the disc 102, 102B during the molding process.

As can be seen in FIGS. 5A and 5B, the inner flange 128, 128B includes a plurality of features 132, 132B. In one embodiment, the features 132, 132B are substantially equally spaced apart from one another and may form a pattern along the entire internal circumference of the rim 104, 104B. In another embodiment, the features 132, 132B are positioned randomly around the inner circumference of the rim 104, 104B. The rim 104, 104B may include any number of features 132, 132B without departing from the intended scope of the present invention. In one embodiment, the inner flange 128, 128B includes at least two features 132, 132B and particularly at least three features 132, 132B. In one embodiment, if an imaginary line $L_I$ were drawn to create an inner circumference of the inner flange 128, 128B that extended equidistantly from the bridge at all points to form an area A between the bridge 116, 116B and the imaginary line $L_I$, the features 132, 132B of the present invention would include between about 5 and about 95% of the area A, particularly between about 15 and about 85% of the area A, and more particularly between about 25 and about 75% of the area A.

The features 132, 132B extend from the bridge 116, 166B at a distance sufficient to hold the disc 102, 102B to the rim 104, 104B. In one embodiment, the features 132, 132B extend between about 0.02 inches (0.051 millimeters) to about 0.15 inches (3.81 millimeters) from the bridge 116, 116B.

The features 132, 132B may be manufactured by any means known in the art. Although FIGS. 4A and 5A and 4B and 5B depict the features 132, 132B as having a tooth shape, the features 132, 132B may take any shape without departing from the intended scope of the present invention. For example, the features 132, 132B may be circular, triangular, pyramids, elliptical or any other shape. In addition, differently shaped features may be used in combination and do not all need to be the same on a particular diaphragm.

Turning back to FIGS. 4A and 5A, when the disc 102 includes apertures 106, the features 132 must extend from the bridge 116 at least to the apertures 106 of the disc 102. In one embodiment, because the rim 104 may not having good adhesion qualities to the disc 102, the features 132 provide a mechanical bond through the disc 102. This is accomplished in conjunction with the plurality of apertures 106 around the outer diameter of the disc 102. The pitch on the apertures 106 and features 132 is such that no matter where the disc 102 is placed in the rim 104 radially, at least one or parts of two apertures 106 line up with the features 132. This can be seen in FIGS. 4A and 5A. The alignment of the apertures 106 and features 132 allows a mechanical bond through each of the features 132 as described above.

In some embodiments, apertures are not needed in the disc. This embodiment is shown, for example, in FIGS. 4B and 5B.

Figure 5C:
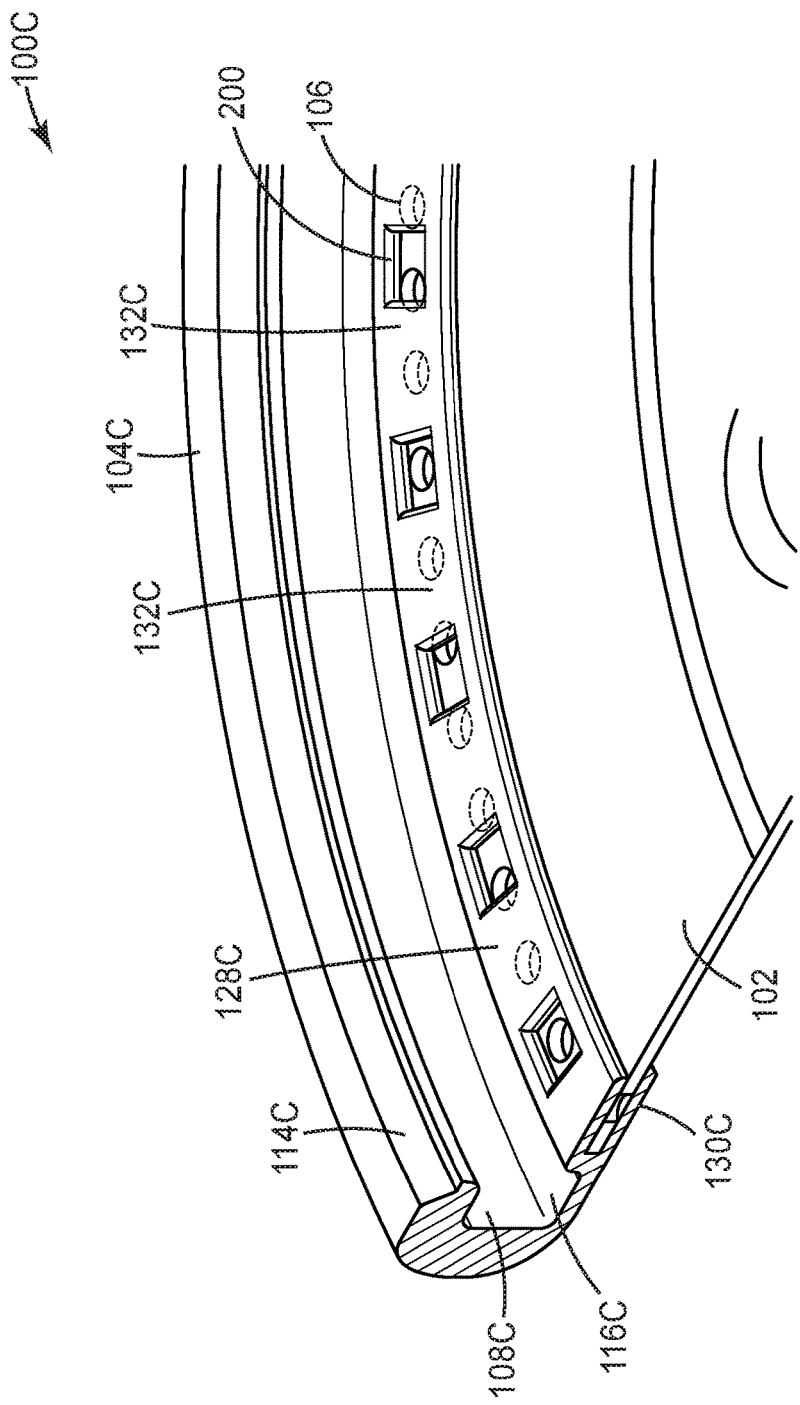
FIG. 5C is an enlarged view of a portion of a third embodiment of a diaphragm of the present invention.

FIG. 5C shows an enlarged view of a portion of a third embodiment of the diaphragm 100C of the present invention. The third embodiment of the diaphragm 100C has many reference characters similar to the reference characters used to describe elements of the first embodiment of the diaphragm 100 except that the reference character "C" has been added. The elements otherwise function similarly. In the embodiments shown and described in FIGS. 4A and 5A and 4B and 5B, the features 132, 132B extend individually from the bridge 116, 116B. In the embodiment shown in FIG. 5C, the inner flange 128C includes a plurality of holes 200 with the features 132C formed in between each of the holes 200. Although FIG. 5C depicts the holes 200 as having a square shape, the holes 200 may be any shape, such as circular, triangular or irregular in shape without departing from the intended scope of the present invention. In one embodiment, the plurality of holes 200 may be equidistant from each other around the periphery of the disc 102C. In other embodiments, the plurality of holes 200 may be randomly spaced from each other. In one embodiment, the features 132C include between about 5 and about 95% of the inner flange 128C, particularly between about 15 and about 85% of the inner flange 128C, and more particularly between about 25 and about 75% of the inner flange 128C. The features 132C in the third embodiment of the diaphragm 100C function similarly to the features 132 of the first embodiment of the diaphragm 100 shown in FIGS. 4A and 5A. Thus, when the disc 102C includes apertures 106, the pitch on the apertures 106 and the features 132C should be such that no matter where the disc 102 is placed in the rim 104C radially, at least one or parts of two apertures 106 line up with the features 132C.

Upon assembly onto the chestpiece, the diaphragm must have enough flexibility to allow the diaphragm to be easily positioned on, and removed from, the chestpiece and rigid enough to ensure that the diaphragm does not unintentionally fall off of the chestpiece. In one embodiment, the rim has a Shore A durometer hardness of between about 40 and about 110, particularly between about 70 and about 90 and more particularly between about 75 and 85.

Although the present invention has been described with reference to preferred embodiments, workers skilled in the art will recognize that changes may be made in form and detail without departing from the spirit and scope of the invention.

What is claimed is:

1. A stethoscope diaphragm comprising:
   a disc; and
   a rim;
      wherein the rim comprises:
         a wall having a first end and a second end,
         a lip extending substantially perpendicularly from the first end of the wall,
         a bridge extending substantially perpendicularly from the second end of the wall, and a fork extending from the bridge;
      a plurality of features extending from the fork; and
         wherein the features are formed from holes cut out from a portion of the fork.

2. The stethoscope diaphragm of claim 1, wherein the plurality of features are spaced substantially equally around an inner circumference of the rim.

3. The stethoscope diaphragm of claim 1, comprising at least three features.

4. The stethoscope diaphragm of claim 1, wherein the disc has a plurality of apertures around an outer periphery of a face of the disc.

5. The stethoscope diaphragm of claim 4, wherein the plurality of apertures are offset from the plurality of features.

6. The stethoscope diaphragm of claim 1, wherein the disc and the rim are a unitary piece.

7. The stethoscope diaphragm of claim 1, wherein the features have a length of between about 0.5 and about 3.8 millimeters from the bridge.

8. A stethoscope diaphragm comprising:
   a disc; and
   a rim, wherein the rim comprises:
      a wall having a first end and a second end;
      a lip extending substantially perpendicularly from the first end of the wall;
      a bridge extending substantially perpendicularly from the second end of the wall;
      a fork extending from the bridge, wherein the fork includes an inner flange and an outer flange; and
      a plurality of features extending from the inner flange; and wherein the features are formed from holes cut out from the inner flange.

9. The stethoscope diaphragm of claim 8, wherein the plurality of features are spaced substantially equally around the inner flange.

10. The stethoscope diaphragm of claim 8, comprising at least three features.

11. The stethoscope diaphragm of claim 8, wherein the disc has a plurality of apertures around an outer periphery of a face of the disc.

12. The stethoscope diaphragm of claim 11, wherein the plurality of apertures are offset from the plurality of features.

13. The stethoscope diaphragm of claim 8, wherein the features have a length of between about 0.5 and about 3.8 millimeters.

14. The stethoscope diaphragm of claim 8, wherein the features comprise between about 5 and about 95% of the inner flange.

\* \* \* \* \*